United States Patent [19]

Zussman et al.

[11] 4,091,223
[45] May 23, 1978

[54] UNSATURATED HYDANTOIN COAGENTS

[75] Inventors: Hyman W. Zussman, Greenwich, Conn.; Martin Knell, Ossining; Martin Dexter, Briarcliff Manor, both of N.Y.

[73] Assignee: Ciba-Geigy Corporation, Ardsley, N.Y.

[21] Appl. No.: 711,200

[22] Filed: Aug. 4, 1976

[51] Int. Cl.² .................. C07D 233/74; C07D 233/80
[52] U.S. Cl. ..................................... 548/308; 548/310; 260/878 R; 260/884; 204/159.17
[58] Field of Search ....................................... 260/309.5

[56] References Cited

U.S. PATENT DOCUMENTS 2,466,177  4/1949  Long ................................ 260/309.5
3,852,302  12/1974  Habermeier et al. ............ 260/309.5

FOREIGN PATENT DOCUMENTS 846,601  8/1960  United Kingdom ............. 260/309.5

*Primary Examiner*—Natalie Trousof
*Attorney, Agent, or Firm*—Luther A. R. Hall

[57] ABSTRACT

Unsaturated hydantoin derivatives of the formula

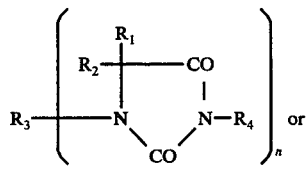

or

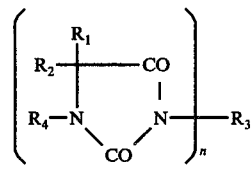

where $R_1$ and $R_2$ are alkyl, $R_3$ is vinyl, allyl, alkylene, substituted alkylene or polyvalent aralkyl, $R_4$ is vinyl or allyl and $n$ is 1 to 3, are coagents for curing polymeric compositions to improve their physical, chemical and electrical properties. These coagents are particularly useful in crosslinking PVC, polyethylene, chlorinated polyethylene and poly(ethylene/vinyl acetate) compositions.

10 Claims, No Drawings

UNSATURATED HYDANTOIN COAGENTS

BACKGROUND OF THE INVENTION

This invention pertains to curable polymeric compositions and in particular to novel curable polymeric compositions containing unsaturated hydantoin derivatives.

Some unsaturated hydantoin derivatives are known. British Pat. No. 846,601 pertains to vinyl derivatives of substituted monohydantoins, processes for preparing these materials and to polymers and copolymers containing such moieties. 3-Vinyl and 1,3-divinyl hydantoin derivatives are described. These materials are homopolymerized or copolymerized with other unsaturated polymerizable molecules. The use of the 1,3-divinyl compounds as crosslinking agents in the copolymerization with other unsaturated compounds is disclosed. Unsaturated bis or tris hydantoins are not suggested.

3-Allyl-5,5-dimethylhydantoin is disclosed by M. Sato, Nippon Kagaku Zasshi, 83, 323 (1962); Chem. Abst. 59, 3908 (1963).

A crosslinking agent is a polyfunctional compound which when incorporated into a polymerizing system enters the polymerizing chains, and by virtue of its polyfunctional nature leads to crosslinked or network structures.

In the free radical polymerization systems, polyfunctional vinyl monomers such as divinylbenzene, ethylene bismethacrylate and triallyl cyanurate are well known as crosslinking agents. British Pat. No. 846,601 suggests that 1,3-divinylhydantoins might be such crosslinking agents as well. These crosslinking agents contain active ethylenic double bonds which react with active ethylenic double bonds in the other monomers present to undergo the crosslinking polymerization reaction.

However, it is known that essentially saturated high molecular weight polymers are often subject to deterioration by thermal, oxidative, light, irradiation or chemical means. Among such polymers are the polyolefins such as polyethylene, polypropylene and the like. These polymeric materials are currently being extensively used as insulation for wire and cable, in conduits, in containers, etc. The fabrication, molding, extrusion, and calendering of these materials is readily accomplished by standard methods. Despite all this, however, the applications of these polymers are circumscribed by their lack of high temperature form stability, that is, their inability to retain a particular shape at elevated temperatures, by their solubility in certain solvents, and by their relatively poor resistance to environmental stress cracking. In U.S. Pat. Nos. 3,264,252 and 3,562,202 it is disclosed that the physical properties of such polymers can be greatly improved by the addition thereto of a minor amount of quinone oxime and curing at a temperature above 170° C. The hydrocarbon insolubility of the polymers is improved and the polymers have increased resistance to creep and to stress cracking.

Chlorinated polyethylene elastomers are well known materials in the rubber art. They are prepared from branched or linear polyethylene by homogeneous solution chlorination or by chlorination of dispersions of finely divided polyethylene in water or other suitable dispersing media. Solution chlorination gives a chlorinated polyethylene of relatively uniform distribution of chlorine atoms on the polymer chain, while dispersion chlorination gives products with a more random distribution of chlorine. Using either method, it is well known that the introduction into the polymer molecule of between 20 and 50% chlorine atoms by weight produces an elastomeric product from polyethylenes which are highly crystalline before chlorination.

Useful elastomeric products must necessarily be vulcanized, or cured by cross-linking. Vulcanization of chlorinated polyethylene has generally been difficult, and the products known as chlorosulfonated polyethylenes, which contain a minor proportion of sulfonyl chloride groups as reactive cross-linking sites are often employed in applications where the simple chlorinated polyethylenes might otherwise be preferred. It has been recommended in the art to vulcanize chlorinated polyethylenes with peroxides, for example, in U.S. Pat. No. 2,534,078, but vulcanizates so obtained are difficult to prepare and have not had physical properties adequate for many uses.

In U.S. Pat. No. 3,531,455 the curing of chlorinated polyethylene composition using an organic peroxide and a polyunsaturated coagent triallyl cyanurate is described to give highly vulcanized products with good properties.

It is well known to promote the peroxide vulcanization or curing of saturated chain polymers by including in the formulation any of a variety of polyunsaturated coagents.

Among the coagents disclosed in the prior art are various maleimides such as N,N'-m-phenylene dimaleimide; allyl esters such as diallyl phthalate, diallyl sebacate, diallyl adipate, allyl methacrylate, diallyl itaconate, triallyl aconitate, diallyl carbonate of diethylene glycol and the like; divinylbenzene, triallyl cyanurate, polybutadiene (1,2), triallyl phosphate, triacryloylhexahydrotriazine, and polyfunctional acrylate or methacrylate esters such as ethylene dimethacrylate, butylene dimethacryate, polyethylene glycol dimethacrylate, trimethylolpropane trimethacrylate, ethylene diacrylate and the like.

The essentially saturated polymers which can be cured with the help of coagents include chlorinated polyethylene (A. R. Guy et al. *Rubber World*, 162(3),60(1970); poly(vinyl chloride) (M. H. Gerard, *Soc. Plast. Eng., Tech. Pap.,* 17, 480 (1971); polypropylene (Japan Patent 71,10664); copolymers of ethylene/vinyl acetate, ethylene/vinyl chloride and ethylene/propylene; chlorosulfonated polyethylene; various rubbers such as nitrile rubber, EPM, EPDM, NBR, SBR and the like.

When peroxide curing is involved, any of the peroxides normally used in curing polymeric systems can be employed. Representative types of peroxides are aryl peroxides, acyl peroxides, aralkyl peroxides, alkyl peroxides and ketone peroxides. Specific examples are dicumyl peroxide and its higher homologues, dibenzoyl peroxide, lauroyl peroxide, succinyl peroxide, methyl ethyl ketone peroxide, n-butyl 4,4'-bis(t-butyl peroxy)-valerate, acetyl peroxide, dicamphoryl peroxide, phthalyl peroxide, tertiary butyl hydroperoxide, ethyl percamphorate, hydroxyalkyl hydroperoxides and other similar organic peroxides or substances which give rise to such peroxides under the hereinafter described reaction conditions. Dicumyl peroxide is preferred because of the fast rate of cure and excellent vulcanizate properties which result from its use.

The use of coagents in the radiation curing of polymers for improved properties is also known, (G. R. Berbeco, *Insulation/Circuits,* 17(2),23(1971)). Radiation processing is carried out by γ-rays from radioisotopes, primarily cobalt-60, or preferably by high-energy electrons from electron accelerators. The same polymers and coagents described under peroxide curing are also used in the radiation curing process. Japan Pat. No. 71,10664 discloses the irradiation curing of polypropylene using the coagent diallyl carbonate of diethylene glycol.

DETAILED DISCLOSURE

This invention pertains to unsaturated hydantoin derivatives which are coagents for curing polymeric compositions to improve their physical, chemical and/or electrical properties.

More particularly, this invention relates to unsaturated hydantoin derivatives of the formula I or II $$\left\{ R^3 \underset{\underset{CO}{\diagdown}}{\overset{\overset{R_1}{\underset{\diagup}{\overline{R_2 \longrightarrow CO}}}}{\longrightarrow}} N-R_4 \right\}_n \quad \text{or} \quad \left\{ R_4-N \underset{\underset{CO}{\diagdown}}{\overset{\overset{R_1}{\underset{\diagup}{\overline{R_2 \longrightarrow CO}}}}{\longrightarrow}} N \right\}_n R_3$$

I  II wherein
$R_1$ and $R_2$ are independently each hydrogen, alkyl of 1 to 6 carbon atoms or phenyl, or $R_1$ and $R_2$ together are alkylene of 4 to 6 carbon atoms,
$R_3$ is vinyl, allyl, alkylene of 1 to 6 carbon atoms, 3-oxapentamethylene, 2-allyloxytrimethylene or polyvalent aralkyl of 8 to 12 carbon atoms,
$R_4$ is vinyl or allyl, and
$n$ is an integer from 1 to 3.

$R_1$ and $R_2$ can independently each be hydrogen or alkyl of 1 to 6 carbon atoms such as methyl, ethyl, isopropyl, sec-butyl, isoamyl and n-hexyl. $R_1$ and $R_2$ can also be each phenyl or together can be alkylene of 4 to 6 carbon atoms such as tetramethylene, pentamethylene or hexamethylene.

Preferably $R_1$ and $R_2$ are independently each alkyl of 1 to 4 carbon atoms or $R_1$ and $R_2$ together are pentamethylene. Most preferably $R_1$ and $R_2$ are each methyl.

When $n$ is 1, $R_3$ is vinyl or allyl. When $n$ is 2 or 3, $R_3$ is alkylene of 1 to 6 carbon atoms such as methylene, ethylene, tetramethylene and hexamethylene. $R_3$ is also 3-oxapentamethylene or 2-allyloxytrimethylene. $R_3$ is also polyvalent aralkyl of 8 to 12 carbon atoms such as p-xylylene and 2,4,6-trimethyl-1,3,5-mesitylylene.

Preferably when $n$ is 2 or 3, $R_3$ is alkylene of 1 to 2 carbon atoms, 2-allyloxytrimethylene, p-xylylene or 2,4,6-trimethyl-1,3,5-mesitylylene.

Compounds of special interest include the unsaturated hydantoin derivatives of formula I or II as hereinbefore defined with the proviso that when $n$ is 1, $R_3$ and $R_4$ cannot both be vinyl.

Accordingly, the compounds of this invention include unsaturated hydantoins of the following structures:

wherein $R_1$, $R_2$ and $R_4$ are as defined above and $R_3'$ is alkylene of 1 to 6 carbon atoms, 3-oxapentamethylene, 2-allyloxytrimethylene or p-xylylene.

Examples of individual compounds of formula I and II include the following:
1,3-divinyl-5,5-pentamethylenehydantoin
1,3-divinylhydantoin
1,3-diallyl-5-ethyl-5-sec-amylhydantoin
1,3-diallyl-5-methyl-5-isobutylhydantoin
1,3-diallyl-5-methyl-5-ethylhydantoin
1,3-diallyl-5-methyl-5-phenylhydantoin
1,3-diallyl-5-ethyl-5-(2-methylbutyl)hydantoin
1,3-diallyl-5,5-pentamethylenehydantoin
1,3-divinyl-5-methyl-5-isobutylhydantoin
1,3-divinyl-5-methyl-5-ethylhydantoin
1,3-divinyl-5-methyl-5-phenylhydantoin
1,3-divinyl-5-ethyl-5-(2-methylbutyl)hydantoin
1-allyl-3-vinyl-5,5-dimethylhydantoin
1,3-diallylhydantoin The invention also pertains to curable polymeric compositions and in particular to curable polymeric compositions containing unsaturated hydantoin derivatives of formula I or II.

More particularly this invention relates to a curable polymeric composition comprising, per 100 parts by weight of, an essentially saturated polymer or mixture of such polymers capable of being cured at elevated temperature in the presence of 1 to 10 parts by weight of an organic peroxide or of being cured by radiation at ambient temperature, and from 0.1 to 10 parts by weight of a compound of formula I or II

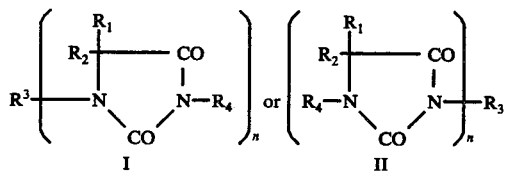

wherein
$R_1$ and $R_2$ are independently each hydrogen, alkyl of 1 to 6 carbon atoms or phenyl, or $R_1$ and $R_2$ together are alkylene of 4 to 6 carbon atoms,
$R_3$ is vinyl, allyl, alkylene of 1 to 6 carbon atoms, 3-oxapentamethylene, 2-allyloxytrimethylene or polyvalent aralkyl of 8 to 12 carbon atoms,
$R_4$ is vinyl or allyl, and
$n$ is an integer from 1 to 3.

Preferably the compounds of formula I or II useful in the curable compositions of this invention are those where $R_1$ and $R_2$ are independently each alkyl of 1 to 4 carbon atoms or $R_1$ and $R_2$ together are pentamethylene; when $n$ is 1, $R_3$ is vinyl or allyl; when $n$ is 2 or 3, $R_3$ is alkylene of 1 to 2 carbon atoms, 2-allyloxytrimethylene, p-xylylene or 2,4,6-trimethyl-1,3,5-mesitylylene, and $R_4$ is vinyl or allyl.

Particularly preferred compounds of formula I or II useful in the curable compositions of this invention are those where $R_1$ and $R_2$ are each methyl. Among the unsaturated hydantoins of this invention exhibiting especially efficacious activity as a curing coagent in the curable compositions are 1,3-divinyl-5,5-dimethylhydantoin, 1,3-diallyl-5,5-dimethylhydantoin, 1,1'-methylene-bis(3-allyl-5,5-dimethylhydantoin), 3,3'-methylene-bis-(1-allyl-5,5-dimethylhydantoin), 2,4,6-tris(3-allyl-5,5-dimethylhydantoin-1-ylmethyl)-mesitylene, 1,3-bis(1-allyl-5,5-dimethylhydantoin-3-yl)-2-allyloxypropane and 1,1'-p-xylylene-bis(3-vinyl-5,5-dimethylhydantoin).

The compounds of formula I or II used as coagents in the compositions of this invention are used at the 0.1 to 10 parts by weight per 100 parts of the essentially saturated polymer or mixture of such polymers to be cured. Preferably the amount of hydantoin coagent used is from 3 to 5 parts by weight per 100 parts by weight of polymer to be cured.

The organic peroxides useful in the curable compositions of this invention are aryl peroxides, acyl peroxides, aralkyl peroxides, alkyl peroxides and ketone peroxides.

Specific examples are dicumyl peroxide and its higher homologues, dibenzoyl peroxide, lauroyl peroxide, succinyl peroxide, methyl ethyl ketone peroxide, n-butyl 4,4'-bis(t-butyl peroxy) valerate, acetyl peroxide, dicamphoryl peroxide, phthalyl peroxide, tertiary butyl hydroperoxide, ethyl percamphorate, hydroxyalkyl hydroperoxides and other similar organic peroxides or substances which give rise to such peroxides under the hereinafter described reaction conditions. Dicumyl peroxide is preferred because of the fast rate of cure and excellent vulcanizate properties which result from its use. The organic peroxides are added in the amount of about 1 to 10 parts by weight per 100 parts of polymer. A preferred amount is about 1.5 to 5 parts. Peroxide present in this quantity is economical and yet provides an adequate rate of cure.

The compositions of this invention can be cured by subjecting them to heat. The temperatures used are those ordinarily employed in the curing of polymeric materials, typically ranging from about 150° to 250° C. The time required for curing the composition will vary with the temperature, activity of the peroxide used, and state of cure desired, but can be routinely determined by one skilled in the art. The cure is generally effected under superatmospheric pressures, however the pressure used is not critical and can vary from about atmospheric to 2000 p.s.i.g. (140 kg/cm$^2$).

The curable compositions of this invention can also be cured by radiation at ambient temperatures. Such radiation is conveniently gamma rays ($\gamma$-rays) from radioisotopes such as cobalt-60 or preferably high-energy electrons produced using electron beam accelerators.

The essentially saturated polymers or mixtures thereof which are capable of being cured at elevated temperatures in the presence of organic peroxides or at ambient temperatures by radiation with $\gamma$-rays or high energy electrons and which are useful in the compositions of this invention include the polymonoolefins such as polyethylene, polypropylene, polybutylene and the like: the copolymers of monoolefins with other monoolefins, or with vinyl acetate, vinyl chloride and the like; chlorinated polyethylene; chlorosulfonated polyethylene; poly(vinyl chloride); and mixtures of blends of such polymers. Of particular importance for use in the wire and cable insulation covering field are poly(vinyl chloride), chlorinated polyethylene, ethylene/vinyl acetate copolymer and blends thereof.

This invention also pertains to the process for curing an essentially saturated polymer or a mixture of such polymers which comprises incorporating into said polymer or mixture of said polymers for each 100 parts by weight of polymer 0 to 10 parts by weight of an organic peroxide and from 0.1 to 10 parts by weight of a compound of formula I or II

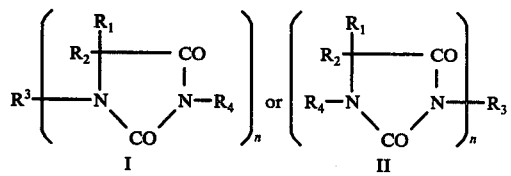

wherein $R_1$ and $R_2$ are independently each hydrogen, alkyl of 1 to 6 carbon atoms or phenyl, or $R_1$ and $R_2$ together are alkylene of 4 to 6 carbon atoms,
$R_3$ is vinyl, allyl, alkylene of 1 to 6 carbon atoms, 3-oxapentamethylene, 2-allyloxytrimethylene or polyvalent aralkyl of 8 to 12 carbon atoms,
$R_4$ is vinyl or allyl, and
$n$ is an integer from 1 to 3, and
subjecting the resultant composition to heat at elevated temperature when an organic peroxide is present or to radiation at ambient temperature in the absence of a peroxide in order to effect curing of the essentially saturated polymer or mixture of such polymers.

Preferably the compounds of formula I or II useful in the curing process of this invention are those where $R_1$ and $R_2$ are independently each alkyl of 1 to 4 carbon atoms or $R_1$ and $R_2$ are pentamethylene; when $n$ is 1, $R_3$ is vinyl or allyl; when $n$ is 2 or 3, $R_3$ is alkylene of 1 to 2 carbon atoms, 2-allyloxytrimethylene, p-xylylene or 2,4,6-trimethyl-1,3,5-mesitylylene, and $R_4$ is vinyl or allyl.

Particularly preferred compounds of formula I or II useful in the curing process of this invention are those where $R_1$ and $R_2$ are each methyl. Among the unsaturated hydantoins of this invention exhibiting especially efficacious activity as a curing coagent in the process of this invention are 1,3-divinyl-5,5-dimethylhydantoin, 1,3-diallyl-5,5-dimethylhydantoin, 1,1'-methylenebis-(3-allyl-5,5-dimethylhydantoin), 3,3'-methylenebis-(1-allyl-5,5-dimethylhydantoin), 2,4,6-tris(3-allyl-5,5-dimethylhydantoin-1-ylmethyl)mesitylene, 1,3-bis(1-allyl-5,5-dimethylhydantoin-3-yl)-2-allyloxypropane and 1,1'-p-xylylene-bis(3-vinyl-5,5-dimethylhydantoin).

The compounds of formula I or II used as coagents in the curing process of this invention are used at the 0.1 to 10 parts by weight per 100 parts of the essentially saturated polymer or mixture of said polymers to be cured. Preferably the amount of hydantoin coagent used is from 3 to 5 parts by weight per 100 parts by weight of polymer to be cured.

The process for curing essentially saturated polymers can be carried out in the presence of 1 to 10 parts by weight per each 100 parts of polymer of an organic peroxide selected from the group consisting of aryl peroxides, acyl peroxides, aralkyl peroxides, alkyl peroxides and ketone peroxides as hereinbefore described. Preferably 1.5 to 5 parts by weight of the organic peroxide is used in the process. Dicumyl peroxide is particularly preferred for its rate of cure and excellent properties resulting from its use.

The process for curing essentially saturated polymers can also be carried out by radiation at ambient temperature using γ-rays from radioisotopes such as cobalt 60 or using high-energy electrons. Radiation from high-energy electrons from an electron beam accelerator is preferred.

METHODS OF PREPARATION

The hydantoins of this invention are in some cases items of commerce, e.g. 5,5-dimethylhydantoin, but they may be made by the classic Bucherer synthesis with potassium or sodium cyanide, ammonium carbonate and a ketone or aldehyde.

$R_1COR_2 + KCN$ (or $NaCN$) + $(NH_4)_2CO_3$

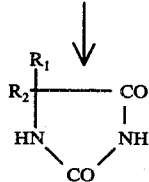

$R_1$ and $R_2$ are as defined above.

The aldehydes and ketones such as acetone, ethyl methyl ketone, cyclohexanone, ethyl sec-amyl ketone, ethyl 2-methylbutyl ketone, butyraldehyde and the like are generally items of commerce.

Unsaturation can be introduced into the hydantoins of this invention in a number of ways.

a. The introduction of vinyl groups can be done by either of two facile methods.

1. Direct Vinylation

This method is described in British Pat. No. 846,601 and involves the reaction of a hydantoin in an inert liquid system with acetylene at elevated temperature in the presence of a vinylation catalyst such as cadmium acetate. This method is used in Example 1 to prepare 1,3-divinyl-5,5-dimethylhydantoin.

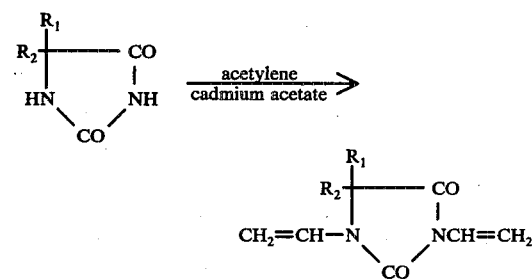

2. Pyrolysis

This method involves first the reaction of the hydantoin with an oxirane to form a β-hydroxyalkyl derivative as seen in U.S. Pat. Nos. 2,381,121 and 3,629,263 followed by esterification and then pyrolysis at very elevated temperature. This method is also exemplified in Example 1.

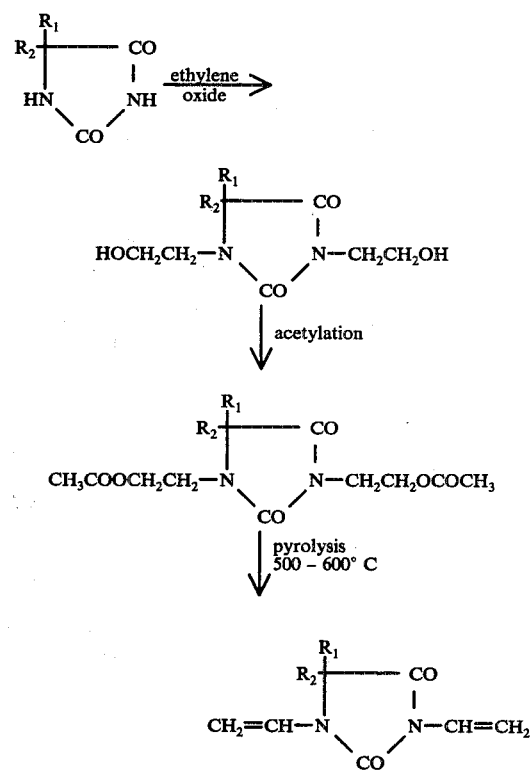

For reasons of economy and ease of operation, direct vinylation would be a preferred process.

b. The introduction of allyl groups is done by use of an allyl halide, preferably allyl chloride, with the hydantoin in the presence of base. Substitution of hydantoin molecules on the 3-N is accomplished easily in the presence of a base such as potassium carbonate as seen in Example 2. Substitution of hydantoin moieties on the 1-N is more difficult and requires the formation of the corresponding alkali metal (preferably sodium) salt using sodium hydride, lithium amide, or the like as seen in Example 3.

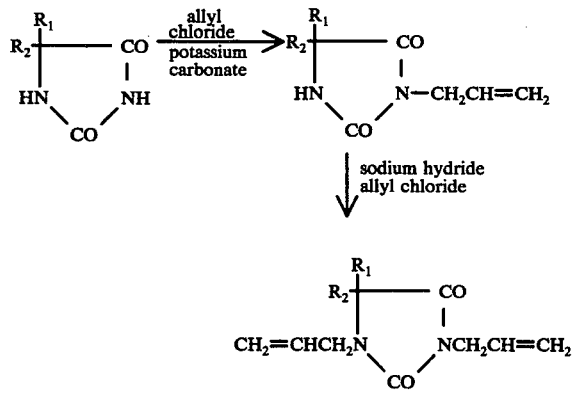

The 1,1-methylene bis-hydantoins used in this invention are prepared by reacting the mono-hydantoin with formaldehyde as seen in U.S. Pat. No. 3,793,248.

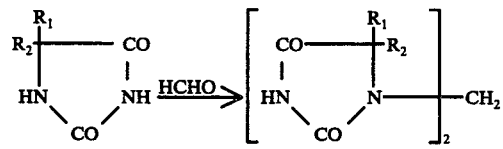

The 3,3-alkylene, oxaalkylene or alkylarylenealkyl bis-hydantoins are prepared by reacting the monohydantoin with the corresponding dihalide, preferably chloride or bromide, in the presence of a base according to the teachings of U.S. Pat Nos. 3,296,208 and 3,542,803.

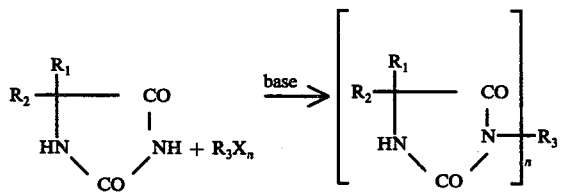

X is chloride or bromide.

UTILITY

The unsaturated hydantoins of formula I or II of this invention are useful as curing agents for polymeric compositions.

The curable polymeric compositions of this invention contain from 0.1 to 10 parts by weight of an unsaturated hydantoin of formula I or II per 100 parts of essentially saturated polymer. Preferably for reasons of economy 3 to 5 parts by weight of the unsaturated hydantoin of formula I or II is sufficient to achieve adequate curing.

When peroxide curing is involved, any peroxide normally used in curing polymers can be employed in this invention. Representative types of peroxides are aryl peroxides, acyl peroxides, aralkyl peroxides, alkyl peroxides and ketone peroxides. Specific examples are dicumyl peroxide and its higher homologues, dibenzoyl peroxide, lauroyl peroxide, succinyl peroxide, methyl ethyl ketone peroxide, n-butyl 4,4'-bis(t-butyl peroxy) valerate, acetyl peroxide, dicamphoryl peroxide, phthalyl peroxide, tertiary butyl hydroperoxide, ethyl percamphorate, hydroxyalkyl hydroperoxides and other similar organic peroxides or substances which give rise to such peroxides under the hereinafter described reaction conditions. Dicumyl peroxide is preferred because of the fast rate of cure and excellent vulcanizate properties which result from its use. The organic peroxides are added in the amount of about 1 to 10 parts by weight per 100 parts of polymer. A preferred amount is about 1.5 to 5 parts. Peroxide present in this quantity is economical and yet provides an adequate rate of cure.

The peroxide-containing compositions of this invention are cured by subjecting them to heat. The temperatures used are those ordinarily employed in the curing of polymeric materials, typically ranging from about 150° to 250° C. The time required for curing the composition will vary with the temperature, activity of the peroxide used, and state of cure desired but can be routinely determined by one skilled in the art. The cure is generally effected under superatmospheric pressures, however the pressure used is not critical and can vary from about atmospheric in 2000 p.s.i.g. (140 kg/cm$^2$).

When radiation curing is involved, the same polymeric formulations containing an unsaturated hydantoin of formula I or II, but without any peroxide component are employed.

The compositions of this invention, containing no peroxide component, are cured by subjecting them to irradiation by γ-rays from a radioisotope such as cobalt-60 or preferably by high-energy electrons from an electron accelerator. The amount of irradiation can be controlled by the energy dose and the time of exposure. Radiation processing is normally carried out under ambient temperatures. Dosage rates to achieve acceptable curing of the compositions of this invention range from 0.1 to 10 megarads. Preferably 3 to 7 megarads of irradiation is sufficient to bring about adequate curing. The presence of an unsaturated hydantoin of formula I or II permits the use of lower dosage levels of irradiation to achieve the same level of curing that is required in the absence of the unsaturated hydantoin coagent.

The compositions of this invention are prepared by conventional methods of mixing, formulating and processing. Various compounding agents such as vulcanization aids, fillers, plasticizers, stabilizers, antioxidants, pigments, carbon black and the like can be used in the compositions of this invention.

The compositions of this invention make possible the safe, rapid and facile curing of essentially saturated polymers by conventional peroxide or radiation processes.

This invention is useful in the manufacture of various items of commerce such as wire covering, cable insulation, hose, films, roofing materials, flashings, molded goods, automotive body panels and the like. Of particular importance are improved wire and cable coverings and automotive body panels.

It is also contemplated that the unsaturated hydantoins of this invention may be useful as the polyene components for photopolymers based on thiol/ene polymer technology. Such photopolymers are used for imaging applications such as in printing plate (Letterflex) preparation, and for a myriad of coating applications such as clear top coats for metal parts, automotive dash panels, UV curable pressure sensitive tape, wire coating, quick drying paints and solder resist coatings for circuit boards. The polymers based on polythiols and polyenes are cured using peroxides or by radiation by ultraviolet light, high energy electrons or γ-rays.

The following examples are presented for the purpose of illustration only and are not to be construed to limit the nature or scope of the instant invention in any manner whatsoever.

EXAMPLE 1

1,3-Divinyl-5,5-dimethylhydantoin

This material may be prepared by reacting acetylene with 5,5-dimethylhydantoin according to the procedure of Example 29 of British Pat. No. 846,601.

Alternatively, 5,5-dimethyl-1,3-divinylhydantoin was prepared by acetylating at 80° C for 2 hours 216 grams (1 mole) of 1,3-bis(2-hydroxyethyl)-5,5-dimethylhydantoin with 408 grams (4 moles) of acetic anhydride in the presence of 20 ml. of pyridine to form the corresponding diacetate ester. Pyrolysis of said diacetate ester by passing through a hot tube at 550° C gave the above product in a 67% yield (at 39% conversion), boiling at 89°–92° C/0.1 mm. (Compound 1).

EXAMPLE 2

3-Allyl-5,5-dimethylhydantoin

To a vigorously stirred mixture of 152 grams (1.1 mole) of potassium carbonate and 128.1 grams (1.0 mole) of 5,5-dimethylhydantoin is 450 ml. of N,N-dimethylformamide (DMF) was added dropwise 84.1 grams (1.1 mole) of allyl chloride over a 50 minute period. The temperature rose exothermically to 66° C, and the reaction mixture was then heated for 2 hours at 60°–70° C. After cooling to room temperature and removing the salt by filtration, a crude product was obtained by evaporation of the filtrate to dryness. The crude product was purified by recrystallization from ether to yield the above named product in a yield of 112.3 grams (67%) melting at 63°–67° C. (Compound 2).

Analysis: Calc'd for $C_8H_{12}N_2O_2$: C,57.13; H,7.19; N,16.66. Found: C,56.92; H,7.24; N,16.76.

EXAMPLE 3

1,3-Diallyl-5,5-dimethylhydantoin

To a slurry of 4.8 grams (0.1 mole) of a 50% sodium hydride mineral oil dispersion in 35 ml. of DMF was added portionwise with stirring 17.6 grams (0.105 mole) of 3-allyl-5,5-dimethylhydantoin. Hydrogen was evolved in this exothermic reaction. The reaction mixture was heated and stirred at 55°–60° C for 1 hour till the gas evolution ceased and a clear solution resulted. To the solution was added dropwise with stirring over a 10-minute period keeping the temperature below 80° C 9.3 grams (0.12 mole) of allyl chloride. The reaction mixture was then heated at 55°–60° C for 1.5 hours. Following cooling to room temperature, the reaction mixture was poured into 100 ml of water. An oily product was formed which was extracted using benzene and purified by vacuum distillation. The above named product was obtained in a yield of 14.15 grams (68%) boiling at 89°–92° C/0.1 mm. (Compound 3).

Analysis: Calc'd for $C_{11}H_{16}N_2O_2$: C,63.44; H,7.74; N,13.45. Found: C,63.75; H,7.85; N,13.52.

EXAMPLE 4

1,1'-Methylene-bis(3-allyl-5,5-dimethylhydantoin)

To a mixture of 13.5 grams (0.05 mole) of 1,1'-methylene-bis(5,5-dimethylhydantoin), prepared in Example 1 of U.S. Pat. No. 2,417,999, and 6.5 gram (0.1 mole) of 86.6% potassium hydroxide in 100 ml of ethanol and 4 ml of water was added dropwise with stirring 12.0 grams (0.157 mole) of allyl chloride over a 10-minute period. The reaction mixture was then refluxed for 30 hours and cooled to room temperature. Salt was removed by filtration, and the filtrate evaporated under vacuum to yield a crude product which was then purified by recrystallization from ether. The above named product was isolated in a yield of 10.6 grams (61%) melting at 97°–101° C. (Compound 4).

Analysis: Calc'd for $C_{17}H_{24}N_4O_4$: C,58.60; H,6.94; N,16.08. Found: C,58.49; H,7.06; N,16.02.

EXAMPLE 5

1,1'-p-Xylylene-bis-(3-allyl-5,5-dimethylhydantoin)

Using the procedure of Example 3, 0.1 mole of the sodium salt of 3-allyl-5,5-dimethylhydantoin was prepared in DMF solution. To the solution at 35° C was added dropwise over a 20-minute period 8.75 grams (0.05 mole) of p-xylylene dichloride dissolved in 24 ml. of benzene. The reaction mixture was then heated for 2.5 hours at 60° C, then cooled and poured into 200 ml. of water. The crude product was separated by filtration, washed with water and then heptane and dried in vacuo over phosphoric anhydride. The material was then purified by recrystallization from isopropanol to give the above named product in a yield of 17.0 grams (78%) melting at 124°–127° C. (Compound 5).

Analysis: Calc'd for $C_{24}H_{30}N_4O_4$: C,65.73; H,6.90; N,12.78. Found: 65.93; H,7.21; N,12.88.

EXAMPLE 6

3,3'-Methylene-bis(1-allyl-5,5-dimethylhydantoin)

Following the procedure of Example 3, 10.7 grams (0.04 mole) of 3,3'-methylene-bis(5,5-dimethylhydantoin), prepared according to Example 1, U.S. Pat. No. 3,296,208, was reacted with 3.8 grams (0.08 mole) of a 50% sodium hydride mineral oil dispersion in 50 ml. of DMF. To the reaction mixture thus formed was added dropwise 6.1 grams (0.08 mole) of allyl chloride. The reaction mixture was then heated at 50°–75° C for 4 hours. After cooling to room temperature and removing the insoluble salt by filtration, the solvent was removed in vacuo to give a viscous oil. The oil was triturated with 75 ml. of hexane to give a crude solid which was purified by recrystallization from ethyl acetate. The above named product was obtained in a yield of 3.8 grams (27%) melting at 107°–115° C. (Compound 6).

Analysis: Calc'd for $C_{17}H_{24}N_4O_4$: C,58.60; H,6.94; N,16.08. Found: C,57.72; H,6.94; N,16.19. NMR spectrum was consistent with expected structure.

EXAMPLE 7

1,3-Bis(1-allyl-5,5-dimethyldantoin-3-yl-(2-allyloxypropane

Using the general procedure of Example 6, 7.2 grams (0.15 mole) of the 50% sodium hydride mineral oil dispersion was reacted in DMF with 15.6 grams (0.05 mole) of 1,3-bis(5,5-dimethylhydantoin-3-yl)-propan-2-ol, prepared according to Example B, U.S. Pat. No.

3,821,243. To the DMF solution was then added dropwise 11.5 grams (0.15 mole) of allyl chloride. The reaction mixture was heated for 2 hours at 60° C and the crude product isolated as a viscous oil as in Example 6. The oil was purified by recrystallization from ether: hexane (1:1) to give the above named product in a yield of 12.9 grams (46%) melting at 48°–57° C. (Compound 7).

Analysis: Calc'd for $C_{22}H_{32}N_4O_5$: C,61.09; H,7.46; N,12.96. Found: C,60,78; H,7.47; N,12.87.

EXAMPLE 8

2,4,6-Tris(3-allyl-5,5-dimethylhydantoin-1-ylmethyl)-mesitylene

Using the procedure of Example 5 by substituting an equivalent amount of 2,4,6-tris(chloromethyl)-mesitylene for p-xylylene dichloride, the above named product was obtained as a crude product melting at 150°–155° C. Recrystallization from isopropanol gave the above named product in a yield of 69% melting at 153°–157° C. A further recrystallization from methanol raised the product melting point to 158°–160° C. (Compound 8)

Analysis: Calc'd for $C_{36}H_{48}N_6O_6$: C,65.43; H,7.32; N,12.72. Found: C,65.43; H,7.74; N,12.58.

EXAMPLE 9

1,1'-p-Xylylene-bis(3-vinyl-5,5-dimethylhydantoin)

Following the general procedure of Example 5, 3-allyl-5,5-dimethyl-hydantoin was replaced by an equivalent amount of 3-vinyl-5,5-dimethylhydantoin, prepared according to Example 1, Brit. Pat. No. 846,601. Reaction with p-xylylene dichloride was carried out at 60°–80° C for 18 hours. An oily product was isolated by pouring the reaction mixture into water and extracting with chloroform. The crude product was purified by recrystallization from isopropanol to give the above named product in a yield of 8.4 grams (41%) melting at 114°–123° C. (Compound 9) Analysis: Calc'd for $C_{22}H_{26}N_4O_4$: C,64.37; H,6.39; N,13.65. Found: C,64.04; H,6.32; N,13.22.

EXAMPLE 10

Coagents in PVC-CPE Blend Formulations

Coagents are used in conjunction with peroxides such as dicumyl peroxide (Di-Cup) to modify the characteristics of crosslinked and/or crosslinkable polymer formulations such as poly (vinyl chloride)-chlorinated polyethylene (PVC-CPE) blends. The effectiveness of the coagent is determined by the degree of crosslinking which occurs.

The coagent compounds were formulated at the 3 phr level into a PVC-CPE blend listed below and milled on a two-roll mill for a total of 5 minutes with 1.8 phr Di-Cup being added after 4 minutes of milling. The front roll of the mill was kept at 135° C and the rear roll at 125° C during this operation. The blended formulations were then compression molded in a press at 175° C for 3 minutes at 1000 psi (70 kg/cm²) and then for 4 minutes at 6000 psi (420 kg/cm²) to prepare 75 mil (1.905 mm) thick plaques. The plaques were then cut into micro tensile bars and their tensile strength measured at 150° C. The tensile strength of the bar at elevated temperatures is a relative measure of the degree of crosslinking, the higher the tensile strength the greater the crosslinking.

| PVC-CPE Blend | |
|---|---|
| PVC (Geon 92, Goodrich) | 100 phr |
| CPE (MX 2243, Dow) | 30 |
| DOP (plasticizer dioctyl phthalate) | 40 |
| Leadstar (stabilizer-lubricant, NL Industries) | 1 |
| Dythal-XL (Stabilizer, NL Industries) | 4 |

Table 1

| 3 phr Coagent plus 1.8 phr Di-Cup | Tensile Strength at 150° C | |
|---|---|---|
| | psi | kg/cm² |
| None | 14 | 0.98 |
| Di-Cup alone | 28 | 1.96 |
| Compound 1 | 42 | 2.94 |
| Compound 3 | 45 | 3.15 |
| Compound 4 | 46 | 3.22 |
| Compound 5 | 28 | 1.96 |
| Compound 6 | 32 | 2.34 |
| Compound 7 | 41 | 2.87 |
| Compound 8 | 42 | 2.94 |
| Compound 9 | 47 | 3.29 |

All of the unsaturated hydantoins tested were effective as coagents in this PVC-CPE peroxide cured blend formulation except Compound 5. Compound 6 exhibited only modest coagent activity.

EXAMPLE 11

Coagents in EVA-CPE Blend Formulations

Coagents are used in the electron beam crosslinking of poly(ethylene/vinyl acetate)-chlorinated polyethylene (EVA-CPE) blends used in wire insulation applications. Polyacrylates and polymethacrylates are currently used in this application even though their electrical properties are marginal for this application.

The coagent compounds were added at the 5 phr level into an EVA-CPE blend listed below and milled on a two-roll mill for a total of 6 minutes. The front roll of the mill was kept at 210° F (99° C) and the back roll at 190° F (88° C) during this operation. The blended formulations were then compression molded in a press with a preheat cycle of 1 minute at 250° F (121° C) and then 2 minutes at 250° F (121° C) and 6000 psi (420 kg/cm²) to yield films of 15 mil (0.38 mm) or 30 mil (0.76 mm) thickness. These films were then irradiated under an electron beam at two dosages, 3 and 7 megarads, respectively. The percent gel in the sample following irradiation indicated the amount of crosslinking which occurred. The higher the gel content, the higher is the degree of crosslinking.

| EVA-CPE Blend | | |
|---|---|---|
| CPE (2243,04, Dow) | 50 | phr |
| EVA (DuPont) | 50 | |
| Drapex 6.8 (Argus Chem. Corp. plasticizer) | 2.5 | |
| Dythal XL (NL Industries, stabilizer-lubricant) | 6.0 | |
| DS 207 (NL Industries, stabilizer-lubricant) | 1.0 | |
| Oncor 23A (NL Industries, flame retardant) | 20 | |
| 2,4,6-tris(3,5-di-tert-butyl-4-hydroxybenzyl)mesitylene (antioxidant) | 1.5 | |

The percent gel was determined by wrapping a sample of known weight (approximately 1 gram) in a stainless steel screen and placing it in a container of refluxing tetrahydrofuran (THF) for 24 hours. The screen containing insolubles was removed, rinsed with THF and dried. The % gel was calculated as follows:

Final wt./Original wt. × 100 = % gel.

It is recognized that the final weight includes some THF insoluble additives used, but this would be the same for all samples so no correction was made and the relative values obtained are valid.

Table 2

| 5 phr Coagent | % Gel, Irradiaton (Electron Beam) | |
|---|---|---|
| | 3 megarads | 7 megarads |
| None | 45.9 | 67.8 |
| Compound 1 | 65.0 | 78.1 |
| Compound 3 | 60.6 | 75.2 |
| Compound 4 | 54.6 | 70.6 |
| Compound 5 | 41.3 | 62.5 |
| Compound 6 | 36.4 | 56.8 |
| Compound 7 | 42.2 | 63.6 |
| Compound 8 | 35.3 | 61.5 |
| TAC* | 54.1 | 74.7 |
| SR 209** | 58.7 | 74.3 |
| SR 350*** | 69.9 | 81.4 |

*TAC is triallyl cyanurate
**SR 209 is tetraethyleneglycol bismethacrylate
***SR 350 is 1,1,1-trimethylolpropane trismethacrylate 1,3-Divinyl-5,5-dimethylhydantoin and 1,3-diallyl-5,5-dimethylhydantoin exhibited excellent coagent activity in the radiation curing of an EVA-CPE blend formulation. Both are superior to triallyl cyanurate and are comparable to the polyfunctional methacrylates used as coagents.

The bis hydantoin, compound 4, performed as a coagent at the overall level of triallyl cyanurate. The other unsaturated hydantoins were less effective as coagents in this radiation curing system in terms of crosslinking as measured by % gel formulation.

EXAMPLE 12

Coagents in EVA-CPE Blend Formulations

The 15 mil (0.38 mm) and 30 mil (0.76 mm) films prepared and radiation cured using 3 megarads of electron beam irradiation as in Example 11 were oven aged at 150° C for 7 days. The % elongation of the cured films before and after aging were measured. A high retention of % elongation after this thermal treatment was desirable.

Table 3

| 5 phr Coagent | Film Thickness mil | Film Thickness mm | % Gel Unaged | % Elongation Unaged | % Elongation Aged | % Retention Elongation Aged |
|---|---|---|---|---|---|---|
| None | 15 | 0.381 | 46 | 420 | 118 | 28 |
| None | 30 | 0.762 | 46 | 506 | 127 | 25 |
| Compound 1 | 15 | 0.381 | 65 | 351 | 143 | 41 |
| Compound 1 | 30 | 0.762 | 65 | 341 | 223 | 57 |
| Compound 3 | 15 | 0.381 | 61 | 366 | 38 | 10 |
| Compound 4 | 15 | 0.381 | 55 | 384 | 50 | 13 |
| TAC* | 15 | 0.381 | 54 | 349 | 65 | 19 |
| SR 350** | 15 | 0.381 | 70 | 257 | 94 | 37 |
| SR 350** | 30 | 0.762 | 70 | 212 | 106 | 50 |

*TAC is triallyl cyanurate
**SR 350 is 1,1,1-trimethylolpropane trismethacrylate A radiation cured EVA-CPE blend containing 1,3-divinyl-5,5-dimethylhydantoin as coagent exhibited excellent absolute levels of % elongation both before and after oven aging for 7 days at 150° C. The % retention of elongation was somewhat superior to the that obtained using the polyfunctional methacrylates and far superior to that obtained using triallyl cyanurate.

Compounds 3 and 4 led to % retention of elongation values comparable to that obtained with triallyl cyanurate.

EXAMPLE 13

Coagents in EVA-CPE Blend Formulations

The 30 mil (0.76 mm) films prepared and radiation cured as described in Example 11 were tested using ASTM D-150 at 1000 megaHertz for dielectric constant (K) and dissipation factor ($D_x$). These data are listed on Table 4.

Table 4

| | Electrical Properties Radiation Cured EVA-CPE Blend Formulation | | | |
|---|---|---|---|---|
| | 3 megarads | | 7 megarads | |
| 5 phr Coagent* | K | Dx | K | Dx |
| None | — | — | 3.68 | 0.016 |
| TAC | 3.65 | 0.018 | 3.29 | 0.018 |
| TAIC | 3.53 | 0.016 | 3.47 | 0.018 |
| SR 350 | — | — | 3.58 | 0.024 |
| SR 351 | 3.51 | 0.018 | 3.34 | 0.018 |
| Compound 1 | 3.34 | 0.019 | 3.36 | 0.018 |
| Compound 3 | 3.28 | 0.019 | 3.72 | 0.017 |
| Compound 4 | 3.32 | 0.015 | 3.37 | 0.017 |

*TAC TAC is triallyl cyanurate
TAIC is triallyl isocyanurate
SR 350 is 1,1,1-trimethylolpropane trismethacrylate
SR 351 is 1,1,1-trimethylolpropane trisacrylate With the exception of the K value at 7 megarads for compound 3, the K and Dx values for the instant compounds indicated better electrical insulating properties than did the control resins including those containing TAC, TAIC, SR 350 and SR 351. Smaller values for K and Dx are desirable for better electrical properties.

What is claimed is:

1. An unsaturated hydantoin of the formula selected from the group consisting of

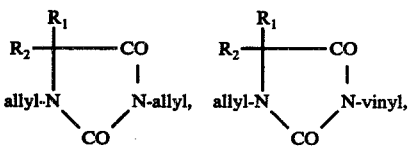

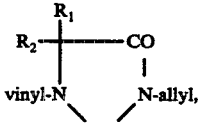

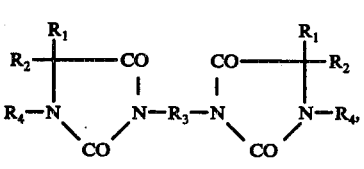

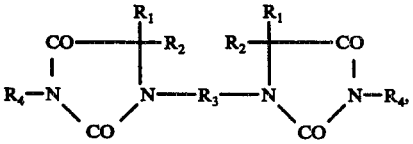

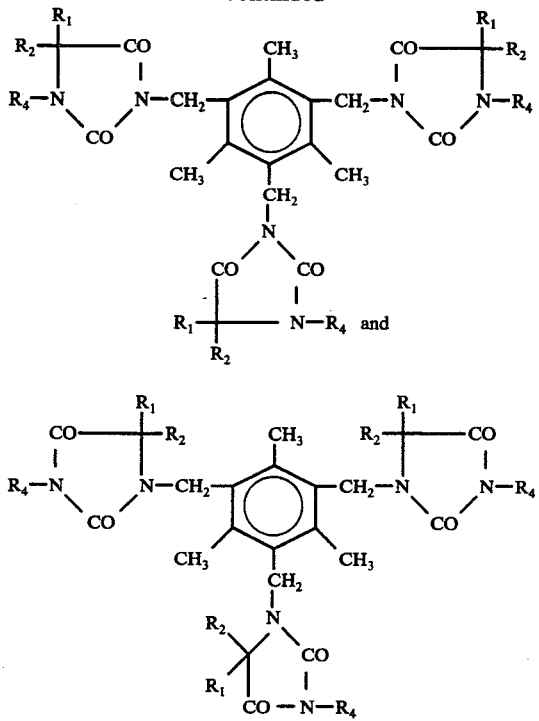

wherein $R_1$ and $R_2$ are independently each hydrogen, alkyl of 1 to 6 carbon atoms or phenyl, or $R_1$ and $R_2$ together are alkylene of 4 to 6 carbon atoms, $R_3$ is alkylene of 1 to 6 carbon atoms, 3-oxapentamethylene, 2-allyloxytrimethylene or p-xylylene, and $R_4$ is vinyl or allyl.

2. A compound according to claim 1 wherein $R_1$ and $R_2$ are independently each alkyl of 1 to 4 carbon atoms or $R_1$ and $R_2$ together are pentamethylene, and $R_3$ is alkylene of 1 to 2 carbon atoms, 2-allyloxytrimethylene or p-xylylene.

3. A compound according to claim 1 wherein $R_1$ and $R_2$ are each methyl.

4. The compound according to claim 1 which is 1,3-diallyl-5,5-dimethylhydantoin.

5. The compound according to claim 1 which is 1,1'-methylene-bis(3-allyl-5,5-dimethylhydantoin).

6. The compound according to claim 1 which is 1,1'-p-xylylene-bis(3-allyl-5,5-dimethylhydantoin).

7. The compound according to claim 1 which is 3,3'-methylene-bis-(1-allyl-5,5-dimethylhydantoin).

8. The compound according to claim 1 which is 1,3-bis(1-allyl-5,5-dimethylhydantoin-3-yl)-2-allyloxypropane.

9. The compound according to claim 1 which is 2,4,6-tris(3-allyl-5,5-dimethylhydantoin-1-ylmethyl)-mesitylene.

10. The compound according to claim 1 which is 1,1'-p-xylylene-bis(3-vinyl-5,5-dimethylhydantoin).

* * * * *